United States Patent [19]

Kitagawa et al.

[11] 4,326,536
[45] Apr. 27, 1982

[54] SPHYGMOMANOMETER

[75] Inventors: Fumio Kitagawa; Tsutomu Ichinomiya, both of Kadoma, Japan

[73] Assignee: Matsushita Electric Works, Ltd., Osaka, Japan

[21] Appl. No.: 128,355

[22] PCT Filed: Nov. 13, 1978

[86] PCT No.: PCT/JP78/00024
§ 371 Date: Jul. 16, 1979
§ 102(e) Date: Jul. 11, 1979

[87] PCT Pub. No.: WO79/00294
PCT Pub. Date: May 31, 1979

[30] Foreign Application Priority Data

Nov. 15, 1977 [JP] Japan .................... 52-138149

[51] Int. Cl.$^3$ .................................. A61B 5/02
[52] U.S. Cl. .................................. 128/682
[58] Field of Search ............... 128/680–683, 128/686

[56] References Cited

U.S. PATENT DOCUMENTS

| | | | |
|---|---|---|---|
| 3,552,383 | 1/1971 | Krueger et al. | 128/682 |
| 3,742,938 | 7/1973 | Stern | 128/687 |
| 3,905,354 | 9/1975 | Lichowsky | 128/681 |
| 3,930,494 | 1/1976 | Maurer et al. | 128/682 |
| 4,026,277 | 5/1977 | Toda et al. | 128/680 |
| 4,058,117 | 11/1977 | Kaspari et al. | 128/682 |
| 4,141,350 | 2/1979 | Shinoda | 128/680 |
| 4,167,181 | 9/1979 | Lee | 128/682 |
| 4,178,918 | 12/1979 | Cornwell | 128/682 |
| 4,188,955 | 2/1980 | Sakamoto et al. | 128/680 |
| 4,216,779 | 8/1980 | Squires et al. | 128/682 |

OTHER PUBLICATIONS

Georgi; H., "Electronic Sphygmomanometer", UK Patent Application GB 2,006,961, publ. May 1979.

*Primary Examiner*—Robert W. Michell
*Assistant Examiner*—Francis J. Jaworski
*Attorney, Agent, or Firm*—Burns, Doane, Swecker & Mathis

[57] ABSTRACT

A sphygmomanometer is provided with an automatic pressure inflation and deflation means for feeding a pressurized air into a cuff wound on the upper arm or the like so as to close the arterial blood flow. Korotkoff's sounds are detected during an interruption of the pressurized air feeding. The air is intermittently repressurized so long as the Korotkoff's sounds can be detected, and is switched over to an exhausting state when the Korotkoff's sounds are no longer detected. The systolic/diastolic blood pressure values are detected during the exhausting state and are digitally indicated. A continuous sound is generated until the Korotkoff's sounds reappear, and thereafter a sound is generated which is synchronized with Korotkoff's sounds.

1 Claim, 10 Drawing Figures

SPHYGMOMANOMETER

TECHNICAL FIELD

This invention relates to sphygmomanometers. More specifically, it relates to a sphygmomanometer which allows measurements of the systolic and diastolic blood pressure values of a person to be measured only by a mounting of a cuff to a portion of the person and a starting operation. This manometer is high in reliability since the measurement never depends on the subjective judgment of a measuring person (or person to be measured) and, for the same reason, the person to be measured is able to measure his own blood pressure value simply and accurately even without having various treatments performed by a doctor or nurse.

BACKGROUND ART

The recent increase in old-age population or in aged individuals easily getting ill has increased the need for diagnoses and the factors accelerating the ageing of individuals, e.g., diabetes, high blood pressures, heart diseases and the like are clearly enumerated, and countermeasures are required to be taken particularly against circulatory organ diseases which are high in the number of deaths and are easy to become chronic. In respect of such diseases, it is of course necessary to give medical treatments, but specialists' guidance of living conditions base on the blood pressure value as a criterion are desirable and, under such circumstances, it is desired to provide a sphygmomanometer with which the blood pressure values can be measured in a simple mnner and accurately.

A standard clinical method of indirectly measuring blood pressures currently employed is based on an auscultatory method by means of Korotkoff's sound.

In this method, air is fed usually at a rate of 20 to 30 mmHg/sec. into a cuff wound on a subject's upper arm having a large artery in the surface skin portion to give an air pressure to the cuff to be 10 to 20 mmHg higher than an anticipated systolic blood pressure value and to press the large artery and stop blood flow therein. Then the air is exhausted usually at a rate of 2 to 3 mmHg/sec. to gradually reduce the air pressure in the cuff; that is, the cuff pressure, the blood flow generated again is known by Korotkoff's sounds and the cuff pressure at this time is measured as the systolic blood pressure value. Incidentally, the Korotkoff's sounds are attenuated vibration sounds having a frequency higher than that of arterial pulse waves, which are produced in the side direction of blood vessel wall at the time when the large artery is slightly opened due to the gradual reduction of the cuff pressure and thus the blood flow of the same arterial pulse wave as that at the time of systole begins to pass through the blood vessel at a high speed and appears as synchronized with the arterial pulse wave. In this method, the cuff pressure when the Korotkoff's sounds appear is made the systolic blood pressure value. When the exhausting of air out of the cuff is further continued, the timing of the appearance of the Korotkoff's sounds appearing as synchronized with the arterial pulse wave at the time of systole (corresponding to peaks of arterial pulse curve) will shift to the side of diastole (corresponding to valleys of the arterial pulse curve) and, at the moment when the korotkoff's sounds appear as synchronized with the diastole is reached, the large artery is already opened so that the blood flow will be no longer throttled and the Korotkoff's sounds will disappear. The cuff pressure at this time is measured as the diastolic blood pressure value.

There are electronic and mechanical types of such sphygmomanometer provided to thus indirectly measure the systolic and diastolic blood pressure values. In these measuring instruments, the appearance and disappearance of the Korotkoff's sounds are detected with one's auditory sense using a microphone or stethoscope, and the pressure indicating value of a mercury or aneroid sphygmomanometer is traced with eyes to be memorized and measured, while increasing and decreasing the pressure to the cuff. Therefore, such measurement depends on the auditory and visual senses so that a skill is required to a measurer for achieving the accuracy. Even if the skill is high, the measuring precision is solely dependent on the subjective judgment of the measurer as described above, so that no accurate measurement will be expected. Further, there is a type of such measuring instrument for use of medical practitioners and specialists that the pressure is automatically increased and decreased but, as the method of increasing and setting the cuff pressure above the anticipated systolic blood pressure value depends on the subjective judgment, there has been a problem that the measuring precision often fluctuates.

OBJECTS AND SUMMARY OF THE INVENTION

A primary object of the present invention is, therefore, to provide a sphygmomanometer wherein the systolic and diastolic blood pressure values can be automatically measured without depending on the subjective judgment of measurers.

Another object of the present invention is to provide a sphygmomanometer wherein the pressure increase and decrease to the cuff for measuring the systolic and diastolic blood pressure values, memorization of the systolic and diastolic blood pressure values, display of them and so on are automatically performed, so that the measurer will be enabled to perform the measurement merely by fitting the cuff to a portion of the body of a subject and performing starting operation, or the blood pressure can be simply and reliably measured even by the subject alone.

A further object of the present invention is to provide a comfortable sphygmomanometer which performs the pressure increase to the cuff while automatically watching the state of blood flow blocking without causing any excessive pressure increase, so that the measurement can be made while the subject feels no pain.

According to the present invention, the above described objects are attained with a sphygmomanometer wherein pressurized air is urged to be fed into a cuff which is wound and fitted to an upper arm or the like of a subject by an automatic pressure inflation and deflation means. The large artery is sensed to be perfectly closed by the cuff inflated by thus feeding the pressurized air thereto. The air in the cuff is gradually exhausted by automatically switching the automatic pressure inflation and deflation means to an exhausting state and the systolic and diastolic blood pressure values are detected to be digitally indicated during this exhuasting step.

THE DRAWINGS

The sphygmomanometer of the present invention shall now be explained further, with reference to accompanying drawings, in which.

DETAILED DESCRIPTION

Figure 1:
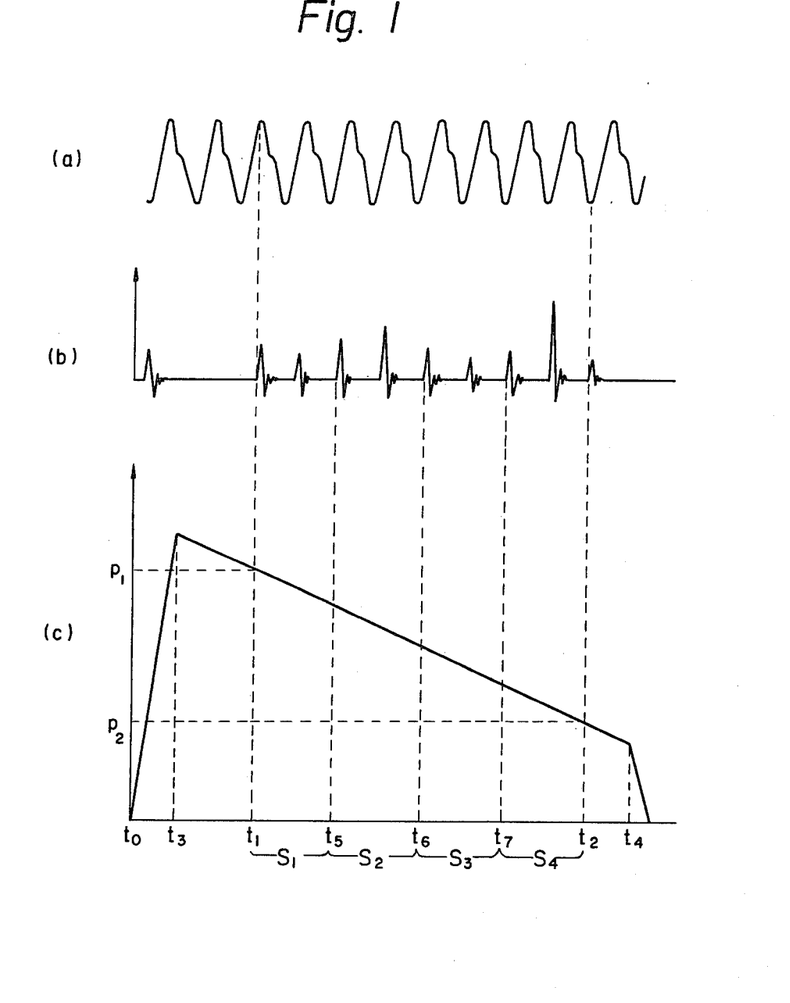
FIG. 1 is an explanatory diagram of general blood pressure measurement.

FIG. 1 explains a standard clinical method of indirectly measuring blood pressures to make it easy to understand the present invention. In the drawing, (a) shows an arterial pulse wave, (b) shows Korotkoff's sounds and (c) shows cuff pressures of the cuff, respectively, and the timings $t_1$ and $t_2$ are respectively timings of the appearance and disappearance of Korotkoff's sounds. The cuff pressure of the cuff 1 is quickly increased to a pressure 10 to 20 mmHg higher than an anticipated systolic blood pressure value between the timings $t_0$ and $t_3$. This quickly pressurizing state is switched at the timing $t_3$ over to a slowly exhausting state and the cuff pressure is gradually reduced until timing $t_4$. When, in the course of such reduction of the cuff pressure, Korotkoff's sounds are produced at the timing $t_1$ for such reason as described above, the cuff pressure $P_1$ at this time will be detected as a systolic blood pressure value and, when the Korotkoff's sounds disappear at the timing $t_2$, the cuff pressure $P_2$ at this time will be detected as a diastolic blood pressure value. Further, by setting the timings $t_5$, $t_6$ and $t_7$ between the timings $t_1$ and $t_2$, the Korotkoff's sound generating period is sectioned into the first to fourth phases $S_1$ to $S_4$.

Figure 2:
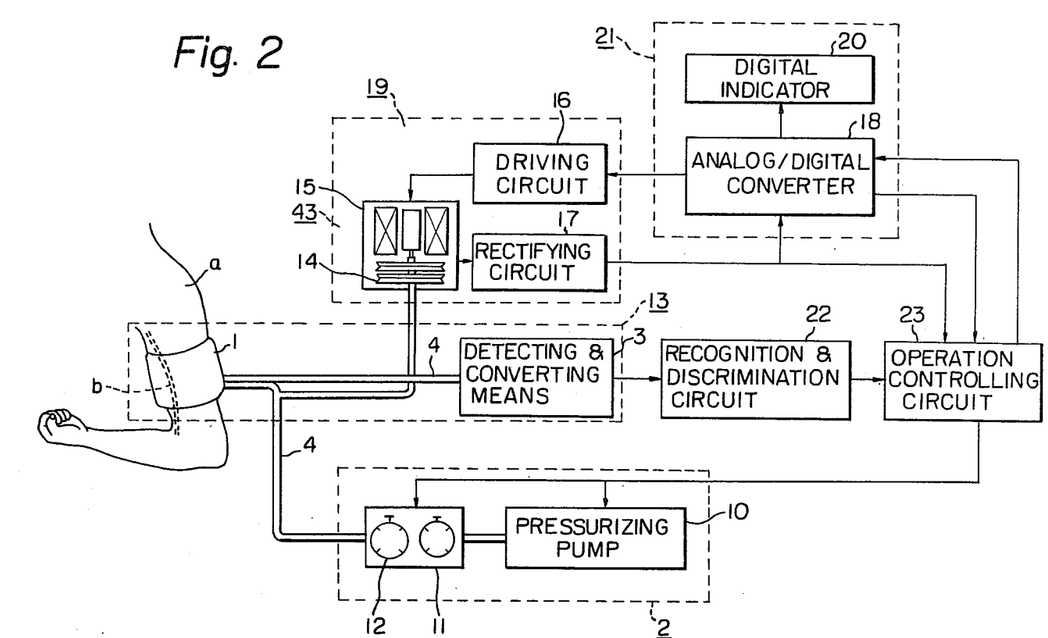
FIG. 2 is a block diagram of an embodiment of the present invention.
Figure 3:
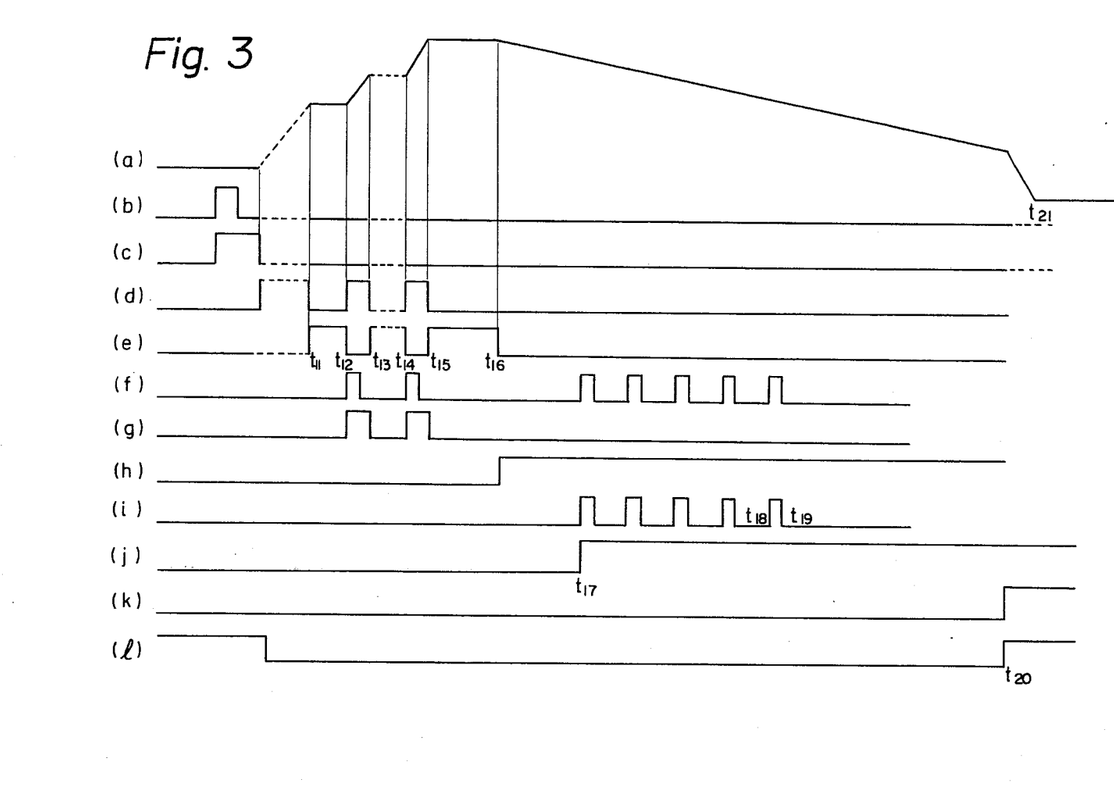
FIG. 3 is a time chart of the same.
Figure 4:
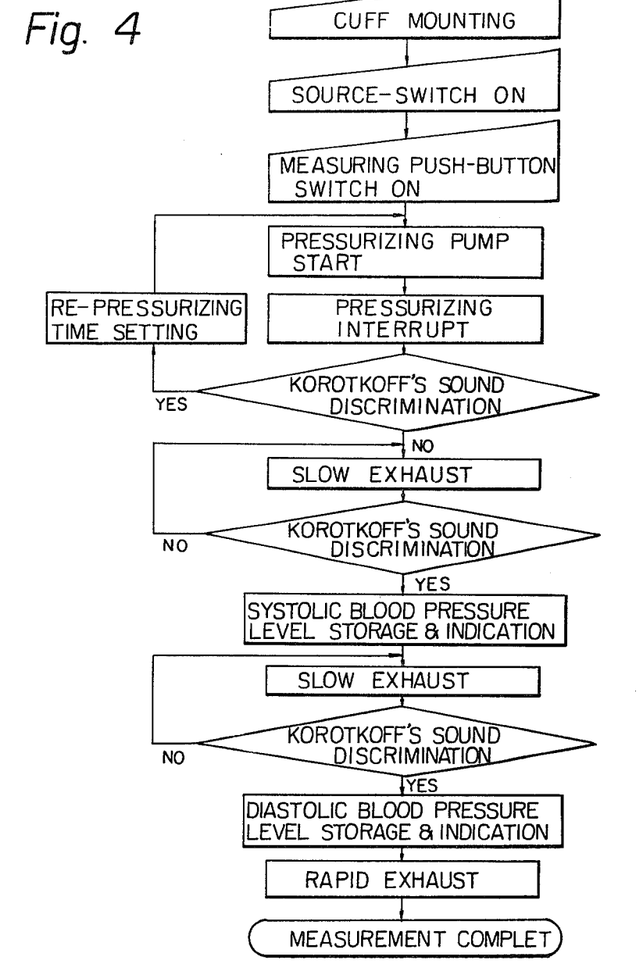
FIG. 4 is a flow chart of the same.

FIGS. 2 to 10 explain an embodiment of the present invention. FIG. 2 is a block diagram of the embodiment of the present invention, FIG. 3 is a time chart of the same, and FIG. 4 is a flow chart of the blood pressure measurement by the same. In the block diagram of FIG. 2, an automatic pressure inflation and deflation means 2 to inflate and deflate the cuff 1 is formed of a pressurizing pump 10, slow exhaust valve 11 and rapid exhaust valve 12, and a Korotkoff's sound detecting section 13 to detect the systolic and diastolic blood pressure values is formed of the above described cuff 1. Korotkoff's sound detecting and converting means 3 is provided with a tube 4 communicating between the cuff 1 and the Korotkoff's sound converting means 3. A pressure-to-signal converting circuit 19 for converting the pressure of the cuff 1 to an electric signal is formed of a diaphragm 14 communicating with the cuff 1 through the tube 4 to detect the cuff pressure and drive a differential transformer 15. A driving circuit 16 drives the differential transformer 15 and a rectifying circuit 17 is provided for converting outputs of the differential transformer 15 corresponding to displaced positions of the diaphragm 14 to a direct current signal and to convert this signal to a digital signal by a later described analog/digital (A/D) converter 18. A storage and indication computing section 21 for storing and indicating the systolic and diastolic blood pressure values comprises an A/D converter 18 for converting the output signal of the rectifying circuit 17 to a digital signal, and a digital indicator 20 having two indicating sections. The output of the Korotkoff's sound detecting section 13 is put into a Korotkoff's sound recognition and discrimination circuit 22, and respective outputs of the recognition and discrimination circuit 22, rectifying circuit 17 and A/D converter 18 are put into an operation controlling circuit 23 for controlling the automatic pressure inflation and deflation means 2 and storage and indication computing section 21.

In the time chart of FIG. 3, (a) shows a pressure state of the cuff, (b) shows an output of a measuring push button switch, (c) shows a resetting signal, (d) shows an operating state of the pressurizing pump 10, (e) shows an operation of a repressurize discriminating gate, (f) shows detected and discriminated Korotkoff's sounds, (g) shows a repressurizing signal, (h) shows an operating state of the blood pressure measuring gate, (i) shows Korotkoff's sound setting pulses of the systolic and diastolic blood pressure values, (j) shows a latch signal for setting the systolic blood pressure values, (k) shows a latch signal rising after a fixed time after disappearance of the Korotkoff's sound setting pulses and making the diastolic blood pressure values unable to be rewritten and (l) shows an operation of the rapid exhaust valve 12.

Referring next to the embodiment of the present invention shown in FIG. 2 with reference to the time chart of FIG. 3 and the flow chart of FIG. 4, the cuff 1 is wound and fitted first of all to the upper arm a of the subject as shown in FIG. 2. Thereafter a current source switch (not illustrated) and measuring push button switch (not illustrated) are switched on in turn so that an output signal of such wave form as shown in (b) of FIG. 3 will be produced by switching on the measuring push button switch, whereby resetting pulses of such wave form as shown in (c) of the drawing will be generated, the slow exhaust valve 11 and rapid exhaust valve 12 will be closed and the circuit will be set in the initial state. At the time when the resetting pulses fall, the pressurizing pump 10 is started and driven as shown in (d) of the drawing so that, as in (a) of the drawing, the cuff pressure of the cuff 1 will begin to quickly rise. The feed of pressurized air at this initial stage is so set as to be about 120 to 130 mmHg. This cuff pressure will be converted to an electric signal in the pressure-to-signal converting circuit 23 so that, as soon as it is detected at the timing $t_{11}$ that the cuff pressure has reached the said level of 120 to 130 mmHg in the operation controlling circuit 23, the drive of the pressurizing pump 10 will be immediately stopped by an output of this operation controlling circuit 23. On the other hand, at the same time when the drive of the pressurizing pump 10 is stopped by this operation controlling circuit 23, the repressurize discriminating gate will open for about 1 to 2 seconds as shown in (e) of FIG. 3 and, when the Korotkoff's sounds are detected and discriminated as in (f) of the drawing while this repressurize discriminating gate is open, a repressurizing signal will be produced simultaneously with the rise of this Korotkoff's sound detecting signal as in (g) of the drawing, whereby the repressurize discriminating gate (e) will be closed and thereafter the pressurizing pump 10 will be driven again. Here, the blood pressure signals collected in the cuff 1 will be converted to electric signals by the detecting and converting means 3 and the Korotkoff's sounds will be recognized and discriminated in the recognition and discrimination circuit 22 and thereafter will be put into the operation controlling circuit 23 so that the generation of the repressurizing signal as well as the setting of the repressurizing time as retaining time of the same, the closing of the repressurize discriminating gate and so on will be performed, and the pressurizing time set as the repressurizing signal generating and retaining time is, for example, about 1 second. When the pressurizing pump 10 is driven by the repressurizing signal, the cuff pressure of the cuff 1 will rise as in (a) of the drawing whereas, when the pressurizing pump 10 is stopped by the fall of the repressurizing signal, the repressurize discriminating gate (e) will open again to detect the Korotkoff's sounds and, when the Korotkoff's sounds are detected, the repressurizing signal will be generated in the same manner as above to perform the repressurizing operation.

After such pressurization as well as Korotkoff's sound detection by means of interruptions of the pressurization are repeated required number of times, the repressurization initiated at the timing $t_{14}$ will end at the timing $t_{15}$, the repressurize discriminating gate (e) is opened at this timing $t_{15}$, at which time the cuff 1 is already pressurized so sufficiently as to have a cuff pressure to perfectly close the large artery b, no Korotkoff's sound will be generated so that no detection and discrimination of the Korotkoff's sound will be performed at the recognition and discrimination circuit 22 and, when a fixed time (about 2 seconds) elapses, the repressurize discriminating gate (e) opened at the timing $t_{15}$ will be automatically closed at the timing $t_{16}$. At the same time, as shown in (h) in FIG. 3, the blood pressure measuring gate will be opened and the slow exhaust valve 11 will be driven to open by the opening signal of this blood pressure measuring gate. Therefore, the air pressure within the cuff 1 will be gradually exhausted at a rate of about 2 to 3 mmHg/sec. and the cuff pressure will be gradually reduced. Such cuff pressure is monitored in the pressure-to-signal converting circuit 19. When the first Korotkoff's sound during the opening period of the blood pressure measuring gate is discriminated and recognized as in (f) of FIG. 3, it will be converted to a Korotkoff's sound setting pulse for measuring the systolic/diastolic blood pressure values as in (h) of the drawing and such latch pulse for setting the systolic blood pressure value as in (j) of the drawing will be generated due to the rise of the first setting pulse (h). Therefore, the cuff pressure value obtained by A/D-converting the output of the pressure-to-signal converting circuit 19 with the A/D converter 18 at the time when the latch pulse (j) rises will be indicated in the digital indicator 20 and this indicated value shows the systolic blood pressure value. On the other hand, the diastolic blood pressure value indicating part of the digital indicator 20 is indicating the cuff pressures as renewed whenever Korotkoff's sounds are discriminated and recognized and, after the setting pulse 11 that has risen at the timing $t_{18}$ falls at the timing $t_{19}$ and when any succeeding setting pulse (i) is not generated, the setting pulse (i) which has risen at the timing $t_{18}$ will be memorized as showing the last Korotkoff's sound and the cuff pressure at the timing $t_{18}$ will be indicated as the diastolic blood pressure value at the digital indicator 20. When the indication of the diastolic blood pressure value thus ends, the operation controlling circuit 23 will operate at the timing $t_{20}$ to generate a latch signal as in (k) of FIG. 3 to make it impossible to rewrite the diastolic blood pressure value and to open the rapid exhaust valve 12 as in (1) of the drawing, whereby the cuff pressure is caused to quickly reduce as in (a) of the drawing and, at the timing $t_{21}$ when the cuff pressure becomes substantially zero, all the operations of the automatic blood pressure measurement are terminated.

Figure 5:
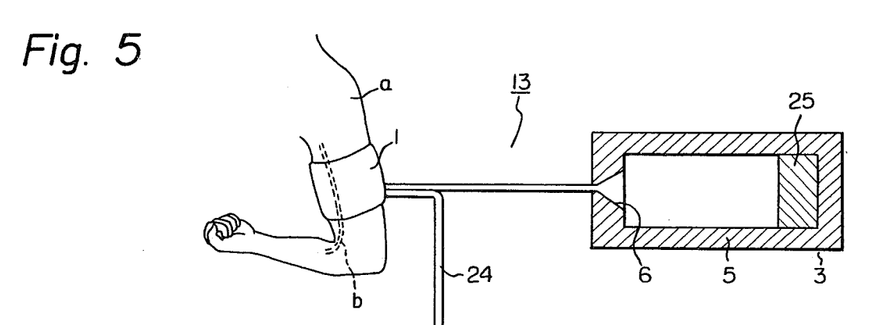
FIG. 5 is a schematic formation view of a Korotkoff's sound detecting section.

FIG. 5 shows an example of practical arrangement of the Korotkoff's sound detecting section 13, wherein the cuff 1 is wound on the upper arm a of a human body so as to block up the artery b is inflated and deflated through a tube 24 connected to the automatic pressure inflation and deflation means 2, a signal sound generated as a slight pressure variation in the artery b will be transmitted to the detecting and converting means 3 through the tube 4 and will be converted to an electric signal, in such that any sound pressure variation transmitted to the detecting and converting means 3 through the tube 4 will be introduced into a housing 5 of the detecting and converting means through a tapered inlet 6 and will be converted to an electric signal by a microphone 25 arranged within the housing. As the inlet 6 which is a connecting part of the tube 4 with the housing 5 of the detecting and converting means is tapered, the detecting and converting means 3 is rendered acoustically to have characteristics of a low range filter and further, as there is provided a space 39 from this inlet 6 to the setting part of the microphone 25, this space is caused to have characteristics of an acoustic band filter, whereby the Korotkoff's sounds can be easily detected and discriminated.

Figure 6:
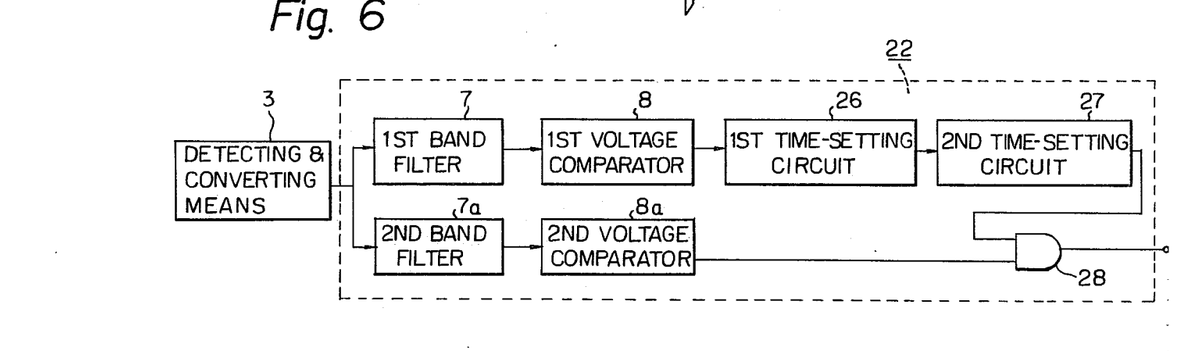
FIG. 6 is a practical block diagram of a Korotkoff's sound recognition and discrimination circuit of the same.
Figure 7:
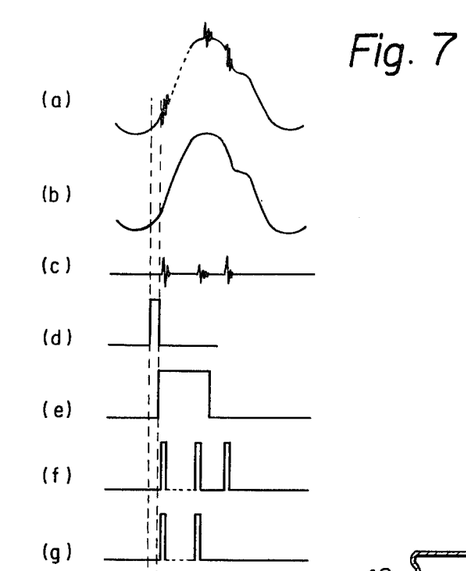
FIG. 7 is a flow chart of the circuit in FIG. 6 of the same.

FIG. 6 shows a more detailed circuit block diagram of the Korotkoff's sound recognition and discrimination circuit 22, and FIG. 7 shows its time chart. In the drawings, such output as shown in (a) of FIG. 7 of the before described detecting and converting means 3 is provided to the first and second band filters 7 and 7a of the recognition and discrimination circuit 22 and is divided into an arterial pulse wave signal of such wave form as shown in (b) of FIG. 7 and a Korotkoff's sound signal of such wave form as shown in (c) of the drawing, these divided signals are subjected to a voltage level detection respectively at voltage comparators 8 and 8a and, only when there are outputs above a fixed level, these voltage comparators 8 and 8a produce outputs. That is, in general, the Korotkoff's sounds have in practice a band of about 20 to 400 Hz with a peak substantially at about 40 Hz, and the frequency tendency near the systolic/diastolic blood pressure fluctuates depending on the differences in individuals, ages, sexes and the like or on low, normal and high blood pressures and can hardly be utilized as a standard for discriminating the blood pressure values. Accordingly, in this embodiment, the Korotkoff's sounds are recognized by the synchronization with the arterial pulse waves, so that such division and detection of the arterial pulse wave signal and Korotkoff's sound signal as shown in (b) of FIG. 7 described above are employed. The outputs of the voltage comparator 8 with which the level of the arterial pulse wave signal is detected are provided to the first time-setting circuit 26, a short pulse-shaped output signal of such wave form as shown in (d) of FIG. 7 is obtained as an output of the first time setting circuit 26 and, putting this output of the first time-setting circuit 26 into the second time-setting circuit 27, such gate controlling signal rising at the rear edge of the output signal (d) of the first time-setting circuit 26 and maintaining an H level for a fixed time as shown in (e) of FIG. 7 will be obtained. Thus the timing of the generation of the gate controlling signal (e) is delayed by the output signal (d), for such reason that the disappearance of the Korotkoff's sound determinative to the diastolic blood pressure value is indefinite depending on the individuals and the Korotkoff's sound may continue to exist even at the starting point of the arterial pulse wave, so that the diastolic blood pressure is discriminated between the timings $t_7$ to $t_2$ in the respective timings $t_1$, $t_5$, $t_6$, $t_7$ and $t_2$ in (c) of FIG. 1, defined as the Swan's recognizing point, in order to prevent any incapability of measurements in such case. Thereafter, the gate controlling signal (e) obtained as an output of the second time-setting circuit 27 is put into an input end of an AND gate 28, the output signal [(f) in FIG. 7] obtained by comparing the voltage of the Korotkoff's sound signal in the voltage comparator 8a is put into the other input end and only the necessary Korotkoff's sound signal pulse is put out as a setting pulse.

Figure 8:
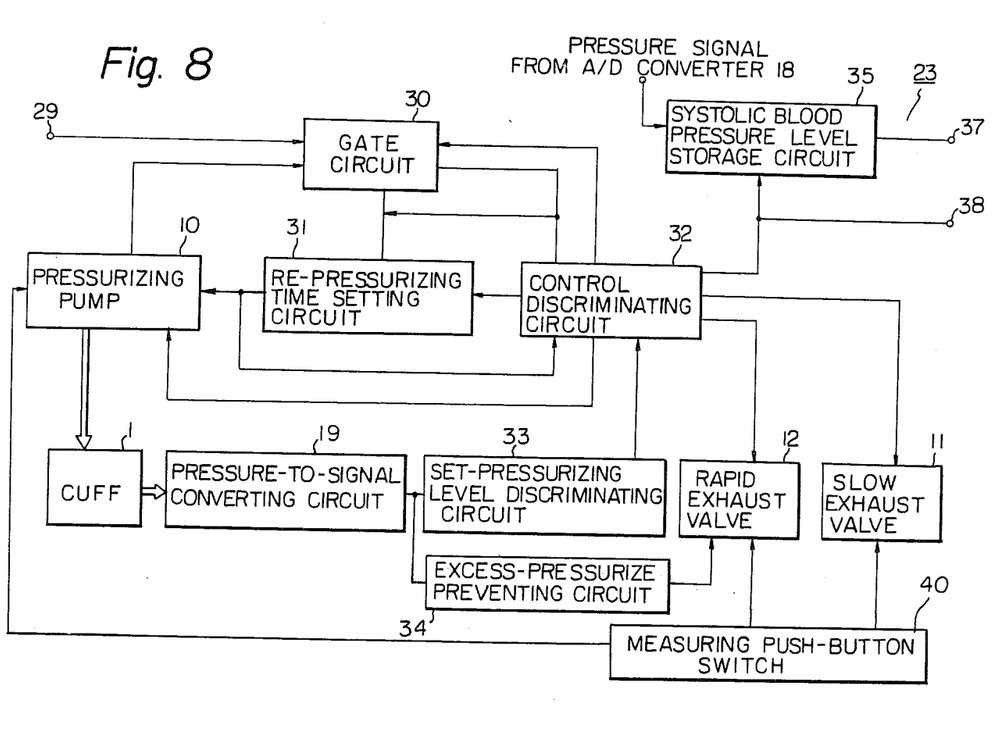
FIG. 8 is a practical block diagram of an operation controlling circuit of the same.

FIG. 8 is a diagram of practical arrangement of the operation controlling circuit 23. Reference numeral 29 indicates an input terminal from the Korotkoff's sound recognition and discrimination circuit 23. The air pressure pressurized by the pressurizing pump 10 is fed to the cuff 1. The output of the gate circuit 30 of the Korotkoff's sound signal is connected to a repressurizing time setting circuit 31 and control discriminating circuit 32. The pressure fed to the cuff 1 is rectified to a direct current in the pressure-to-signal converting circuit 19 and its output is connected to a set pressurizing level discriminating circuit 33 and excess pressurization preventing circuit 34. A systolic blood pressure level storage circuit 35 sends a Korotkoff's sound setting signal of the systolic blood pressure value discriminated in the control discriminating circuit 32. At this time, the pressure signal from the A/D converter 18 as stored in the systolic blood pressure level storage circuit 35 is sent to an indication output terminal 37 and is indicated as the systolic blood pressure value in the digital indicator 20. On the other hand, the Korotkoff's sounds appearing following the systolic blood pressure value Korotkoff's sound are sent to a terminal 38 as a data rewriting signal of the systolic blood pressure value until they disappear, and the cuff pressure at this time is indicated at the digital indicator 20 while being renewed for each input of the Korotkoff's sound as a temporary diastolic blood pressure value. The rapid exhaust valve 12 will operate when the measurement is reset, the pressurization is in excess or the measurement is completed, and its initial operation is performed by means of a measuring push button switch 40. Further, at the same time as the blood pressure measuring gate opens in the control discriminating circuit 32, the slow exhaust valve 11 is operated to slowly exhaust air out of the cuff 1. This valve 11 is also reset initially by the measuring push button switch 40.

In the circuit of FIG. 8, the measuring push button switch 40 as pushed causes the respective circuits to be reset and set to be in the initial state. At the same time as the rapid exhaust valve 12 and slow exhaust valve 11 are closed, the pressurizing pump 10 will start. Therefore, a pressurized air will be fed into the cuff 1 wound on the upper arm a, its pressure will be converted to an electric signal in the pressure-to-signal converting circuit 19 and, when the set pressurization value of 120 to 180 mm. Hg is reached, the set pressurizing level discriminating circuit 33 will come to operate, which is discriminated by the control discriminating circuit 32 to set off the pressurizing pump 10. When the pressurizing pump 10 stops, the Korotkoff's sound gate circuit 30 is opened and the presence of Korotkoff's sounds is checked. If the Korotkoff's sounds are present at this time, a pulse of about 1 second is generated from the repressurizing time setting circuit 31, the pressurizing pump 10 will be actuated and the cuff 1 is again pressurized. At the same time, the repressurizing discriminating gate timer of the control discriminating circuit 32 is forcibly reset. When the repressurization ends, the Korotkoff's sound gate circuit 30 will again open in the same manner and the presence of Korotkoff's sounds will be checked. If the pressurization to the cuff 1 is already such as to block up the artery b, there will be no presence of Korotkoff's sounds and, therefore, when about 2 seconds elapse, the repressurizing discriminating gate timer in the control discriminating circuit 32 generates gate pulses for the blood pressure measurement, whereby the gate of the repressurizing time setting circuit 31 is made to be off, as well as the pressurizing pump 10 off. Now, if blood pressure measuring gate pulses are generated in the control discriminating circuit 32, the slow exhaust valve 11 will open and the pressure of the cuff 1 will be gradually exhausted. In the course of this gradual exhausting Korotkoff's sounds will appear, but the systolic to diastolic blood pressure value setting values are produced by taking an AND of the Korotkoff's sounds and blood pressure measuring gate pulses. Thereby, the first appearing Korotkoff's sound is latched in the systolic blood pressure level storage circuit 35 and is provided to the indication output terminal 37. In the same manner, the following appearing Korotkoff's sound is provided to the indication output terminal 38 as a data rewriting signal of the diastolic blood pressure value until the sound disappears. When the generation of Korotkoff's sounds disappears, the rapid exhaust valve 12 is opened about 2 seconds later and the residual pressure of the cuff 1 is exhausted. The excess pressurization preventing circuit 34 will open the rapid exhaust valve 12 under a pressure of about 250 to 260 mm. Hg in order to prevent the cuff 1 from being pressurized in excess in an event when any abnormality arises in the signal system which is operating the pressurizing pump 10. The design is further made so that, when the current source is set off, the rapid exhaust valve 12 is opened to render all on the safe side.

Figure 9:
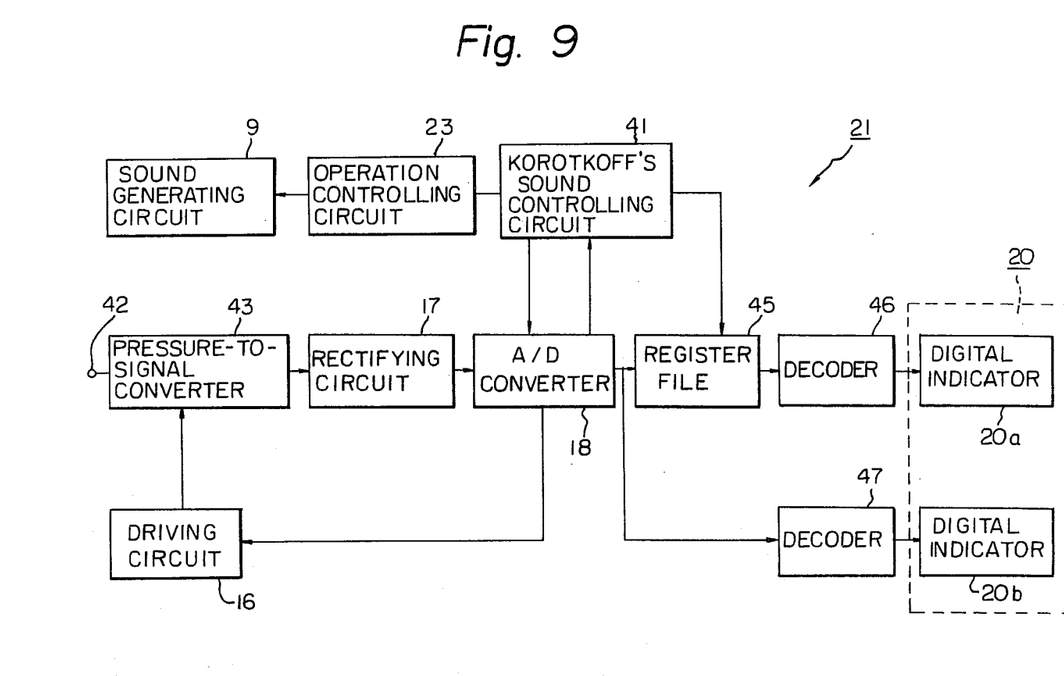
FIG. 9 is a practical block diagram of a storage and indication computing section.

FIG. 9 shows a practical arrangement of the storage and indication computing section 21. In the drawing, a sound generating circuit 9 is so made as to be operated by a signal from the operation controlling circuit 23 in order to make the blood pressure measuring state known by sounds. A Korotkoff's sound controlling circuit 41 provides signals for determining the maximum/minimum blood pressure values. In such case, a pressure signal transmitted to a cuff pressure input terminal 42 is converted to an electric signal in the pressure-to-signal converter 43 which comprises the diaphragm 14 and differential transformer 15 and sequentially to a direct current in the rectifying circuit 17. The differential transformer 15 in the pressure-to-signal converter 43 is fed with a required driving signal from the A/D converter 18 and a driving circuit 16 is provided as a differential transformer driver in order to amplify this signal. Then, the systolic blood pressure value signal discriminated in the Korotkoff's sound controlling circuit 41 is stored in a register file 45. The register file 45 performs write-in and read-out in response to digit signals from the A/D converter 18 and its output signal is subjected to a code conversion performed by a decoder 46. In the same manner, a signal determining the diastolic blood pressure value is provided from the A/D converter 18 and is subjected to a code conversion at a decoder 47. The thus code-converted signals of the decoders 46 and 47 are indicated respectively by numerical indicating sections 20a and 20b in the digital indicator 20. In the circuit of the embodiment of FIG. 9, the Korotkoff's sounds of the systolic/diastolic blood pressure values discriminated in the operation controlling circuit 40 control the storage and indication of the pressures of the systolic/diastolic blood pressure values in the Korotkoff's sound controlling circuit 41 in order to be further separately indicated by the numerical indicating sections 20a and 20b. That is, the pressure detected at the pressure-to-signal converter 43 is converted to an electric amount in the differential transformer 15 and its signal is converted to a direct current in the rectifying circuit 17 to be an input to the A/D converter 18. In the A/D converter 18, the direct current signal is made to be a digital code of BCD and is simultaneously synchronized with a digit signal provided from the A/D converter 18, so as to latch the register file 45 together with a Korotkoff's sound controlling signal from the Korotkoff's sound controlling circuit 41. This register file 45 is a kind of memory comprising a flip-flop. Therefore, the systolic blood pressure value stored in the register file 45 is converted to a code by the decoder circuit 46 of a BCD-7 segment and appears in the numerical indicating section 20a and, in the same manner, the diastolic blood pressure value having a latch memory within the A/D converter 18 rewrites and latches a BCD output of the A/D converter 18 until the Korotkoff sounds disappear by using the Korotkoff's sounds appearing in the Korotkoff's sound controlling circuit 41. Therefore, this latched output of the A/D converter 18 is converted to a code in the decoder 47 of the BCD-7 segment and appears in the numerical indicating section 20b. A sound generating circuit 29 generates, when the pressurizing pump 10 stops and the blood pressure measuring state is reached, a sound with a continuous sound generating signal notifying that the measurement is initiated. When the Korotkoff's sounds begin to appear, intermittent sounds are generated to reduce any measurement errors. Further, a differential transformer driver 44 produces and amplifies a signal of 2 KHz upon the digit signal of the A/D converter 18 and provides the signal to the differential transformer 15.

Figure 10:
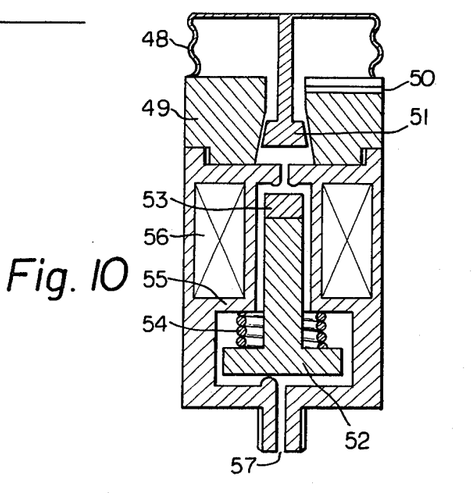
FIG. 10 is a schematic formation view of a slow exhaust valve of the same.

FIG. 10 shows the slow exhaust valve 10 in the automatic pressure inflation and deflation means 2, wherein a bellows 48 is connected to a mount 49 and the mount 49 is provided with an exhaust port 50. A regulating valve 51 is connected to the bellows 48. A plunger 52 has a rubber packing 53 connected to its tip. A spring 54 is inserted between the mount 55 and the plunger 52. A coil 56 operates electromagnetically the plunger 52. A pressure input port 57 is provided below the plunger. Therefore, in the slow exhaust valve 11 of FIG. 10, a pressure applied to the cuff 1 is connected to the input port 57 of the slow exhaust valve 11. At this time, the slow exhaust valve 11 is open as no current is passed.

The pressure is applied at this time to the bellows 48 and, when the pressure is high, the bellows 48 expands so that the regulating valve 51 will be pulled up in the direction of constriction, whereby the exhaust air volume is reduced. When the pressure becomes low, the expansion of the bellows 48 is reduced so that the regulating valve 51 will lower, and the exhaust air volume is increased. Therefore, when the pressure is either high or low, the exhausting rate is substantially constant. That is, at the time of measuring the blood pressures, generally, an air pressure is kept applied to the cuff 1 wound on the upper arm a and the cuff pressure is gradually reduced, the cuff pressure at the time when a Korotkoff's sound is initiated to be heard on the artery b on the distal side of the upper arm a is made to be the systolic blood pressure value and the cuff pressure at the time when the sound becomes to be unheard is made to be the diastolic blood pressure value, but it is not desirable to measure the blood pressure by exhausting the air of the pressure in the cuff 1 too slowly, because a congestion of blood will occur in the subject. If, to the contrary, the blood pressure is measured with the pressure of the cuff too quickly exhausted, the measuring time can be reduced but the measuring precision becomes low. Further, if the air pressure applied to the cuff 1 is gradually exhausted, the exhausting rate will be high when the pressure within the cuff is high but, as the pressure within the cuff 1 becomes gradually lower, the exhausting rate also becomes lower so that errors in detecting the Korotkoff's sounds will occur. It is generally medically recognized, therefore, that in order to accurately measure the blood pressures the pressure being applied within the cuff 1 should be gradually exhausted at a rate of 2 to 3 mm. Hg/sec. and the Korotkoff's sound appearing at each arterial pulse wave should be detected. For this purpose, the slow exhaust valve 11 of such structure as shown in FIG. 10 is adopted so that air can be exhausted out of the cuff 1 at a constant rate and yet gradually.

In som, there is provided an inflation and deflation means for feeding the pressurized air into the cuff wound on an upper arm or the like until the artery is perfectly closed. Such means is automatically switched over to an exhausting state to gradually exhaust the pressurized air out of the cuff after the artery is perfectly closed. This is achieved during the step of feeding the pressurized air into the cuff by detecting the Korotkoff's sounds at the time when the feeding is interrupted, and intermittently repeating the feeding so long as the Korotkoff's sounds can be detected. The pressurizing means is switched over to the exhausting state when the Korotkoff's sounds can be no longer detected. In the case of detecting the Korotkoff's sounds to recognize the systolic/diastolic blood pressure values, the gate pulses are delayed for a fixed time from the starting point of the arterial pulse wave and lasting for a predetermined time period so that the Korotkoff's sounds will be detected during the period of these gate pulses.

In the case of discriminating an output signal of the Korotkoff's sound detecting and converting means, this output signal is provided to the filter and then to the voltage comparator to improve the interruption characteristic by this filter.

The sound generating circuit section generates continuous sounds during the exhaust period until the Korotkoff sounds are detected. Sounds synchronized with the Korotkoff's sounds are then generated when the Korotkoff's sounds are initiated.

We claim:

1. A sphygmomanometer comprising:

first means for selectively feeding pressurized air into a cuff wound on an upper arm or the like and exhausting air from said cuff, second means connected to the cuff for detecting Korotkoff's sound, automatic control means operably connected to said first and second means for:

actuating said first means in a manner pressurizing said cuff to a given pressure, sensing the output of said second means to detect the presence of Korotkoff's sound signals at said given pressure, reactuating said first means in response to said sensing of Korotkoff's sound signals, from said second means to repressurize said cuff at least once to an increased pressure level, sensing the output of said second means to detect the disappearance or presence of Korotkoff's sound signals at said increased pressure level, switching said first means to an exhaust mode to depressurize said cuff in response to the sensed disappearance of Korotkoff's sound signals, and means for detecting and digitally indicating the systolic and diastolic blood pressure values during said exhaust mode, said indicator means including sound generating means for generating continuous sounds during said exhaust mode until the reappearance of Korotkoff's sounds and thereafter generating sounds synchronized with Korotkoff's sounds.

* * * * *